United States Patent
Kobayashi et al.

(10) Patent No.: US 6,656,733 B1
(45) Date of Patent: Dec. 2, 2003

(54) METHOD FOR EFFICIENTLY PRODUCING REDIFFERENTIATED PLANTLETS BY ADDITION OF THICKENING AGENT

(75) Inventors: Takeshi Kobayashi, Nagoya (JP); Hiroyuki Honda, Nagoya (JP); Eiji Nagamori, Nisshin (JP)

(73) Assignee: President of Nagoya University, Nagoya (JP)

( * ) Notice: Subject to any disclaimer, the term of this patent is extended or adjusted under 35 U.S.C. 154(b) by 0 days.

(21) Appl. No.: 09/488,747

(22) Filed: Jan. 21, 2000

(30) Foreign Application Priority Data

Aug. 25, 1999 (JP) ............................................. 11-238485

(51) Int. Cl.⁷ .............................. C12N 5/09; A01H 4/00
(52) U.S. Cl. .................... 435/430; 435/421; 435/430.1; 435/420
(58) Field of Search ................................. 435/410, 420, 435/430.1, 430

(56) References Cited

U.S. PATENT DOCUMENTS

| | | | |
|---|---|---|---|
| 5,008,200 A | * | 4/1991 | Ranch et al. .......... 435/240.49 |
| 6,080,913 A | * | 6/2000 | Tarczynski et al. ......... 800/298 |
| 6,080,920 A | * | 6/2000 | Holton .................... 800/323.3 |

FOREIGN PATENT DOCUMENTS

| | | |
|---|---|---|
| JP | 62-198334 | 2/1987 |
| JP | 6-46838 | 2/1994 |
| JP | 6-327368 | 11/1994 |
| JP | 7-196410 | 8/1995 |
| JP | 8-140513 | 6/1996 |
| JP | 9-220036 | 8/1997 |

OTHER PUBLICATIONS

Ye, et al., Acta Botanica Sinica, (1993) vol. 35, No. Suppl., pp. 83–87.*
Singha, 1982, J. Amer. Soc. Hort. Sci., 107:657–600.*
Mackay et al., 1988, HortSci., 113(2):282–287.*
Li et al., In Vitro Cellular and Developmental Biology—Plant, 1998, vol. 34, No. 1, pp. 22–26.*
Siegler, D.S., "Hydrogels, Gums and Pectins", Feb. 2002, Plant Biology 263, Plants and Their Uses, pp. 1–5.*

* cited by examiner

*Primary Examiner*—Irene Marx
(74) *Attorney, Agent, or Firm*—Oblon, Spivak, McClelland, Maier & Neustadt, P.C.

(57) ABSTRACT

The method of producing a redifferentiated plantlet of the present invention comprises a step of proliferating cultured plant cells in a liquid medium containing a thickening agent and a step of redifferentiating the cultured plant cells after the proliferating step.

11 Claims, No Drawings

METHOD FOR EFFICIENTLY PRODUCING REDIFFERENTIATED PLANTLETS BY ADDITION OF THICKENING AGENT

BACKGROUND OF THE INVENTION

The present invention relates to a method for efficiently producing a large amount of plantlets by means of tissue culture using differentiation totipotency of a plant.

When dedifferentiated cells obtained by tissue culture of a plant are cultured under appropriate conditions, redifferentiation of organs can be induced to regenerate a complete plant. Up to now, numerous studies have already been made on a method of producing a redifferentiated plant such as a plantlet by using a tissue culture technique. Examples of the studies include "development of medium suitable for growth promotion" (Jpn. Pat. Appln. Publication No. 7-196410), "study on culture conditions" (Jpn. Pat. Appln. Publication No. 9-220036), "utilization of substance released from plant" (Jpn. Pat. Appln. Publication No. 6-327368), and "development of culture medium" (Jpn. Pat. Appln. Publication No. 8-140513). However, the studies on medium and culture conditions must be separately performed for each plant species. Therefore, these approaches have a drawback since its general applicability is low. Then, to obtain the redifferentiated plant such as a plantlet in a large amount, it is desired to develop a widely applicable, efficient, and simple method of producing the redifferentiated plantlet by using the tissue culture technique.

BRIEF SUMMARY OF THE INVENTION

An object of the present invention is to provide a method of producing a redifferentiated plant such as an adventive embryo and plantlet, efficiently in a large amount in a short period.

To attain the aforementioned object, in the present invention, a thickening agent was added to a growth medium for cultured plant cells. As a result, it was found that the number of redifferentiated plantlets was increased. It has never been reported that productivity of the redifferentiated plantlets is improved by addition of the thickening agent, as is the case of the present invention.

The method of producing a redifferentiated plantlet of the present invention comprises a step of proliferating cultured plant cells in a liquid medium containing a thickening agent and a step of redifferentiating the cultured plant cells after the proliferating step.

DETAILED DESCRIPTION OF THE INVENTION

Now, the efficient production method for a redifferentiated plantlet of the present invention will be explained in detail.

The method of the present invention comprises a first step of proliferating cultured plant cells in a liquid medium containing a thickening agent and a second step of redifferentiating the cultured plant cells after the proliferating step. In this case, the culture of the first step is called "growth culture" and the culture of the second step is called "redifferentiation culture".

The type of plant cell to be used in the efficient production method for a redifferentiated plantlet of the present invention is not particularly limited. Any type of cell may be used as long as it can be redifferentiated into an individual plant. Furthermore, the type of cell may be derived from any species and may be a cultured cell induced from any site of a plant. The cultured cells for producing the redifferentiated plantlet may be subcultured cells in a state of callus, or any cells already cultured in a liquid culture medium. Alternatively, protoplasts may be used. Of them, it is preferable to use the cultured cells maintained in a liquid medium such as cultured carrot cells. Note that induction of the callus, preparation of the liquid-cultured cells, and preparation of the protoplasts can be performed by a conventionally-known method to those skilled in the art, more preferably, by appropriately modifying it if necessary.

The liquid medium for use in culturing and proliferating cultured cells is not particularly limited, and any culture medium may be used as long as the cultured cells can be proliferated. In general, preferably used is an aqueous medium containing Murashige-Skoog medium (Murashige T. and Skoog. F (1962) Physiol. Plant. 15, 473) as a main component and a requisite sugar and plant hormones, etc. as additives. As the sugar, for example, sucrose is added to a basic medium such as the Murashige-Skoog medium in an amount of, e.g., 10–50 g/L. As the plant hormones, auxins and cytokinins are used. As the auxins, 2,4-dichlorophenoxy acetic acid may be used in an amount of 0.05–5 mg/L. As the cytokinins, kinetin may be used in an amount of 0.05 to 0.5 mg/L. The medium to be used preferably has pH 5.0–6.5.

In the present invention, the thickening agent contained in the medium is not particularly limited, and any thickening agent may be used as long as it increases a viscosity of the medium and has no adverse effect upon growth of the cultured cells. Examples of the thickening agent include sodium alginate, propylene glycol alginate ester, carboxymethyl cellulose, methyl cellulose, carboxymethyl starch, sodium polyacrylate, guar gum, xanthan gum, and locust bean gum. Preferably, sodium alginate and carboxymethyl cellulose may be used. The thickening agent may be added by dissolving it in a medium when the medium is prepared.

The concentration of the thickening agent in the medium can be appropriately set within a range from a concentration imparting a viscosity to the medium to a concentration imparting a viscosity with no effect upon growth of the cultured cells. For example, sodium alginate or carboxymethyl cellulose may be contained in an amount of 0.05–0.5 (w/v) %, and preferably in an amount of 0.1–0.2 (w/v) %.

In the present invention, the step of culturing/ proliferating the cultured cells in a liquid medium containing the thickening agent can be aseptically carried out in accordance with a known method in the art. For example, cells are cultured in an MS medium containing plant hormones and a sugar while gyrating or shaking. This growth culture is performed preferably at a gyration speed (or shaking speed) of 50–200 rpm (or 50–200/min) at a temperature of 20–30° C. under dark conditions.

In the present invention, the growth culture is performed for 10 to 20 days. Thereafter, the cultured cells are transferred to a redifferentiation culturing step.

In the present invention, the step of redifferentiating the cells proliferated in the growth medium in accordance with the aforementioned method, can be carried out by appropriately modifying a known method to those skilled in the art depending upon a type of cultured cells. Generally, to induce redifferentiation, the cultured cells are inoculated to a medium (redifferentiation medium), whose composition of plant hormones are different from that in the growth medium and suitable for inducing redifferentiation.

The medium (redifferentiation medium) with the composition of the plant hormones suitable for redifferentiation must be studied and selected depending upon a type of the cultured cells. For example, as a redifferentiation medium for cultured carrot cells, it is possible to use a medium which is the same as the growth medium mentioned above except that plant hormones is eliminated, as will be described later. When the cultured carrot cells are inoculated to the redifferentiation medium excluding the plant hormones and then cultured in the medium, the cultured cells are regenerated into organs (stem, leaf, and root) via an adventive embryo.

Besides the aforementioned method for producing a redifferentiated plantlet by eliminating the plant hormones in the growth medium, in another plant species, another method may be used. In this method, redifferentiation of organs such as stem, leaf, and root may be sequentially induced by using auxins and cytokinins in combination and by changing the quantity ratio thereof.

In a case where redifferentiation is induced, the culture conditions must be also studied as to whether or not they have preferable effects upon the redifferentiation with respect to individual plant species and selected based upon the results of the studies.

For example, in carrot cultured cells, the redifferentiation culture step is carried out under light conditions as will be described later.

According to the production method of the present invention, the cultured cells are first grown in the medium containing a thickening agent for a period. Then, the resultant cultured cells are transferred to the redifferentiation culturing step. Thereafter, the number of redifferentiated plantlets is counted. The counted number is compared with that of a control grown in a medium containing no thickening agent. In this manner, effect of the present invention can be demonstrated.

EXAMPLES

Effect of Sodium Alginate Added Upon Liquid Redifferentiation of Carrot Callus

The carrot callus is usually cultured in a liquid growth medium containing Murashige-Skoog (MS) medium as a main component and plant hormones as additives (this step is called "growth culture"), and then the resultant culture s are inoculated to the same growth medium except that the plant hormones are not contained (this step is called "redifferentiation culture") to regenerate it into plantlets under light conditions. This is called as "a liquid redifferentiation experiment".

1. Materials and Methods

Embryogenic callus was used which was induced from a young carrot plant (Daucus carota L. cv. US-Harumakigosun). As the growth medium, an MS medium of pH 5.8 was used which contained 0.1 mg/L of 2, 4-dichlorophenoxy acetic acid (2, 4-D) and 0.2 mg/L of kinetin, and 20g/L of sucrose. The callus was placed in a 500-mL Erlenmeyer flask containing 150 mL of the growth medium and the callus suspension was cultured on a gyratory shaker at a speed of 100 rpm. On day 14 after initiation of culturing, the callus was collected and transferred to a redifferentiation medium (the same medium as the growth medium except that the plant hormones were not contained), and then cultivation for regeneration was carried out under light conditions (light intensity 35 $\mu$mol/m$^2$s, 14h/d) while gyrating in the same manner as above. The number of regenerated plantlets (plantlet having a shoot of 1 mm or more) obtained after 11 days of initiation of the redifferentiation culture was counted.

2. Results

The carrot callus was cultured in the growth medium containing sodium alginate in an amount of 1.6 g/L and thereafter transferred to the redifferentiation medium containing no sodium alginate. The effect of sodium alginate was observed. The results are shown in Table 1.

TABLE 1

Table 1: Effects of Sodium Alginate added

| Type of sodium alginate | Number of redifferentiated plantlets after 11 days |
| --- | --- |
| Sodium alginate A (100–150 cp) | 4200 |
| Sodium alginate B (300–400 cp) | 7600 |
| Sodium alginate C (500–600 cp) | 7600 |
| No additives (Control) | 3500 |

Three types of commercially available sodium alginates different in molecular weight (estimated by a viscosity in 1% solution and represented by numbers parenthesized (e.g., 100–150 cp) in Table 1) were added to a growth medium. In any case, it was confirmed that sodium alginate is effective in increasing the number of redifferentiated plantlets.

Furthermore, to confirm the effect of another thickening agent, carboxymethyl cellulose (CMC) was likewise added to a growth medium in the same concentration (0.16% by weight) as sodium alginate. As a result, a redifferentiation frequency increased to about 2.2 folds in the same as in the case of sodium alginate (data are not shown). From these results, it is considered that the effect of the addition of sodium alginate is not due to a biological effect but the ability of preventing collision between callus by increasing the viscosity of the medium.

When the mechanism of preventing collision as mentioned above is effective, this method for increasing the redifferentiation frequency by adding a thickening agent can be widely and generally applied to the cases where redifferentiated plantlets are produced via an adventive embryo. When the same experiment was performed with respect to a rice plant callus, a redifferentiation frequency increased approximately twice. As a result, it is presumed that this method is generally applicable to cultured plant cells.

According to the present invention, it is possible to provide a method for producing a redifferentiated plant such as an adventive embryo and a plantlet, efficiently in a short time. The method of the present invention is also simple since it produces an effect simply by adding a thickening agent such as sodium alginate to a conventionally-used culture medium without using a specific apparatus. In addition, as long as cells have a redifferentiation potency, redifferentiated plantlets can be increased in number by adding a thickening agent to a growth medium. Therefore, the method of the present invention can be widely and generally applicable to all cells having redifferentiation potency.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A method of producing a redifferentiated plantlet comprising proliferating rediffertiated cultured plant cells in a liquid medium containing a thickening agent selected from the group consisting of sodium alginate and carboxymethylcellulose and redifferentiating the cultured plant cells after the proliferating step.

2. The method of claim 1, wherein the thickening agent is sodium alginate.

3. The method of claim 1, wherein the thickening agent is carboxymethylcellulose.

4. A method of producing a redifferentiated plantlet comprising proliferating redifferentiated cultured plant cells in a liquid medium containing a thickening agent that is selected from the group consisting of sodium alginate, propylene glycol alginate ester, carboxymethyl cellulose, methyl cellulose, carboxymethyl starch, sodium polyacrylate, guar gum, xanthan gum, and locust bean gum; and redifferentiating the cultured plant cells after the proliferation step.

5. The method of claim 4, wherein the thickening agent is propylene glycol alginate ester.

6. The method of claim 4, wherein the thickening agent is methyl cellulose.

7. The method of claim 4, wherein the thickening agent is carboxymethyl starch.

8. The method of claim 4, wherein the thickening agent is sodium polyacrylate.

9. The method of claim 4, wherein the thickening agent is guar gum.

10. The method of claim 4, wherein the thickening agent is xanthan gum.

11. The method of claim 4, wherein the thickening agent is locust bean gum.

\* \* \* \* \*